(12) United States Patent
Epstein et al.

(10) Patent No.: US 9,510,898 B2
(45) Date of Patent: *Dec. 6, 2016

(54) ABLATION METHOD

(71) Applicant: Halt Medical, Inc., Brentwood, CA (US)

(72) Inventors: Gordon Epstein, Pleasanton, CA (US); Bruce Lee, Pleasanton, CA (US); Russell Delonzor, Pleasanton, CA (US); Adam Hagmann, Pleasanton, CA (US); Richard Spero, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,605

(22) Filed: Aug. 18, 2013

(65) Prior Publication Data

US 2015/0066020 A1     Mar. 5, 2015

Related U.S. Application Data

(63) Continuation of application No. 13/069,466, filed on Mar. 23, 2011, now Pat. No. 8,512,330, which is a (Continued)

(51) Int. Cl.
*A61B 18/14* (2006.01)
*A61B 18/18* (2006.01)
*A61B 18/00* (2006.01)

(52) U.S. Cl.
CPC .......... *A61B 18/1477* (2013.01); *A61B 18/18* (2013.01); *A61B 2018/00559* (2013.01); *A61B 2018/00577* (2013.01); *A61B 2018/00648* (2013.01); *A61B 2018/143* (2013.01); *A61B 2018/1425* (2013.01); *A61B 2018/1432* (2013.01); *A61B 2018/1475* (2013.01)

(58) Field of Classification Search
CPC .............. A61B 18/02; A61B 18/00577; A61B 18/1477; A61B 2018/00791; A61B 2018/00839; A61B 2018/00875; A61B 2018/0212; A61B 2018/0225; A61B 2018/0262; A61B 2018/1465

See application file for complete search history.

(56) References Cited

U.S. PATENT DOCUMENTS 5,810,804 A * 9/1998 Gough et al. .................. 606/41
7,419,487 B2 * 9/2008 Johnson et al. ............... 606/41
(Continued)

*Primary Examiner* — Michael Peffley
(74) *Attorney, Agent, or Firm* — Handal & Morofsky LLC

(57) ABSTRACT

A method of ablating a uterine fibroid using a particular trocar is disclosed. The trocar comprises a plurality of ablation stylets. The trocar is adjustable to assume a plurality of configurations, each of the configurations having the stylets extended to a different extent from the trocar. A region to he ablated is imaged, The size of the region to be ablated is noted. The size of the region to be ablated is compared to a matrix of known ablation regions, each of the known ablation regions being associated with one of the configurations of the particular trocar. The region to be ablated is associated with a most nearly matching known ablation region by comparison of the region to be ablated to the known ablation regions. A trocar is inserted into the uterine fibroid at a position, which more closely matches the position of the particular trocar with respect to the known ablation region. The stylets are deployed from the trocar to an extent corresponding to the configuration.

12 Claims, 4 Drawing Sheets

Related U.S. Application Data continuation-in-part of application No. 11/429,921, filed on May 8, 2006, now Pat. No. 8,512,333, which is a continuation-in-part of application No. 11/173,928, filed on Jul. 1, 2005, now Pat. No. 8,080,009.

(56) References Cited

U.S. PATENT DOCUMENTS

| | | | |
|---|---|---|---|
| 2004/0215182 A1* | 10/2004 | Lee | 606/32 |
| 2004/0254572 A1* | 12/2004 | McIntyre et al. | 606/41 |
| 2005/0107781 A1* | 5/2005 | Ostrovsky et al. | 606/41 |

* cited by examiner

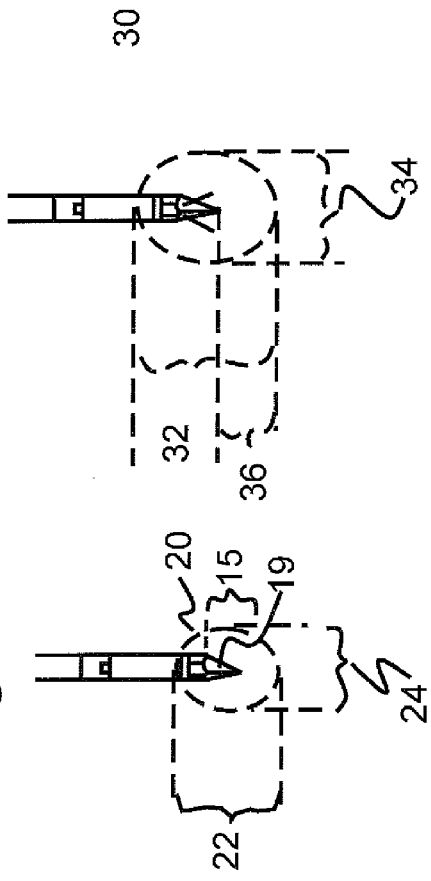
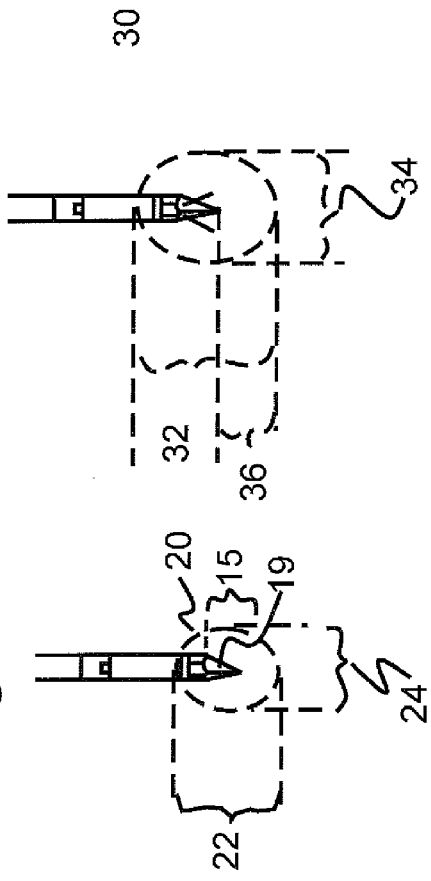
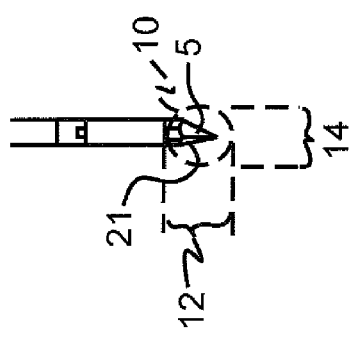
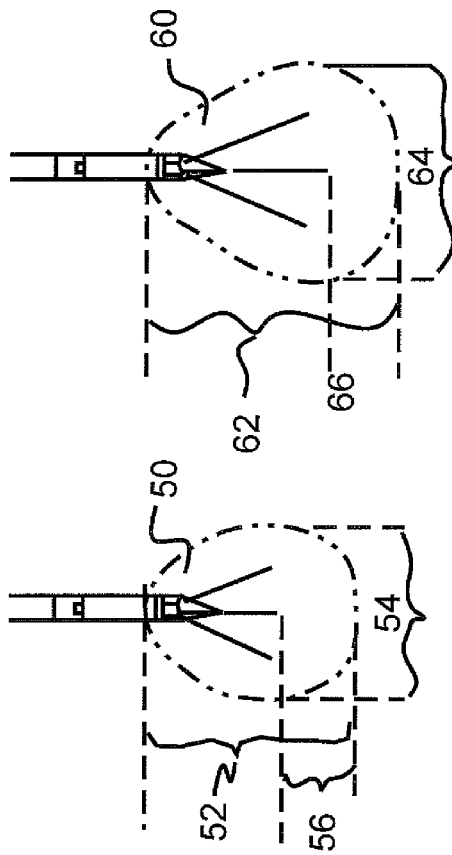
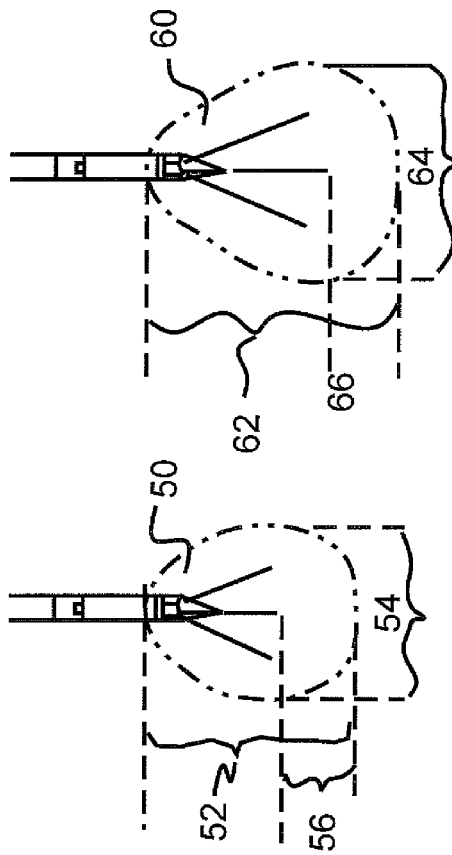
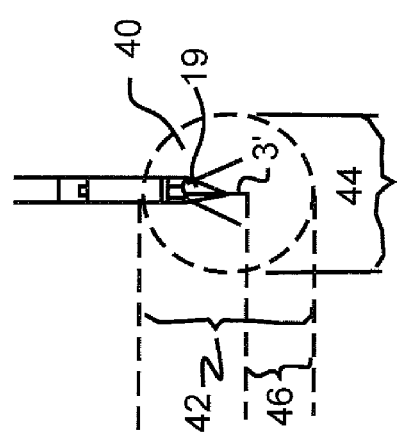

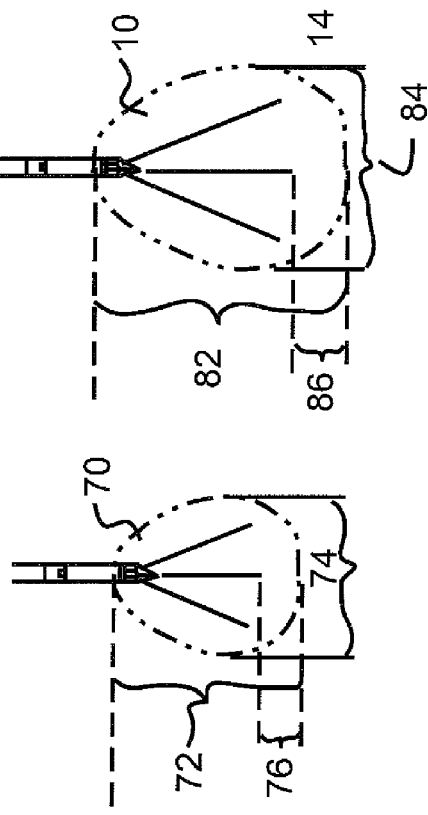
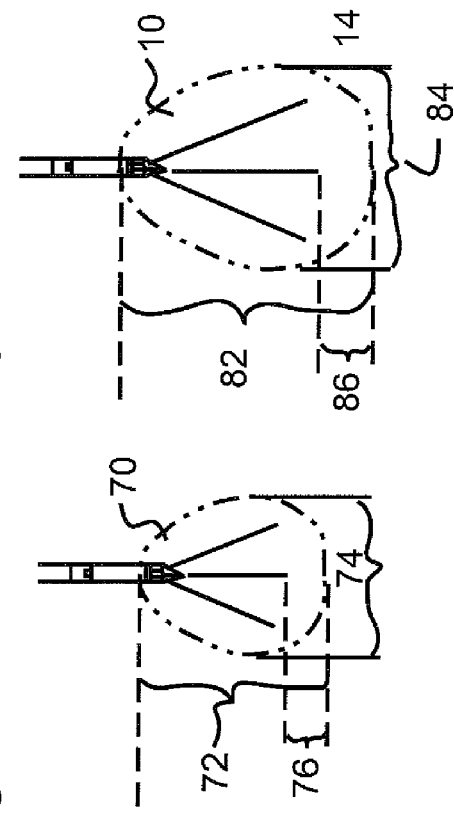
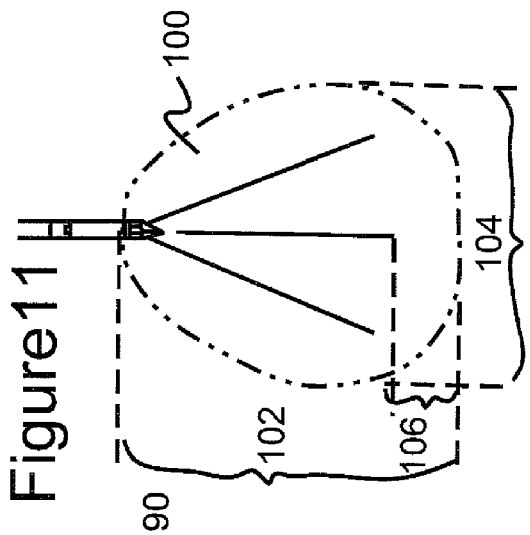
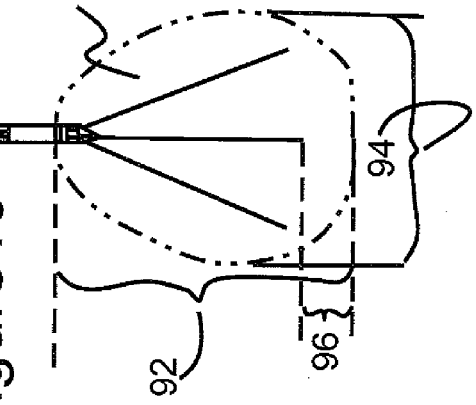

ABLATION METHOD

CROSS REFERENCE TO RELATED APPLICATIONS

This application is a continuation of U.S. patent application Ser. No. 13/069,466,now U.S. Pat. No. 8,512,330,filed Mar 23, 2011, and entitled Ablation Method, which is a continuation in part of U.S. patent application Ser. No. 11/429,921, now U.S. Pat. No. 8,512,333,filed May 8,2006, and entitled Anchored RF ablation device for the destruction of tissue masses, which in turn is a continuation in part of U.S. patent application Ser. No. 11/173,928, now U.S. Pat. No. 8,080,009,entitled Radio Frequency Ablation Device for the Destruction of Tissue Masses filed on Jul. 1, 2005, the disclosures of which are incorporated herein by reference.

TECHNICAL FIELD

The invention relates to apparatus and methods for uterine fibroid ablation, and, in particular, to structures and methods for achieving fibroid tissue destruction in volumes with largely predictable orientations, dimensions and configurations.

STATEMENT REGARDING FEDERALLY SPONSORED RESEARCH OR DEVELOPMENT (Not applicable)

BACKGROUND OF THE INVENTION

Every year in the United States, approximately 230,000 women undergo hysterectomies for removal of uterine fibroids. In addition, it has been estimated that likely another six million women in the United States with uterine fibroid symptoms prefer to suffer, rather than taking on the risks and inconveniences associated with hysterectomy, the standard treatment and a major surgery that always results in infertility. This situation is much the same in the other parts of the world where women are in need of a safe alternative to hysterectomy.

Alternatives to hysterectomy such as uterine artery embolization (in which the blood supplies to the arteries that feed the fibroids are cut off), and Myomectomy (which involves a surgical removal of the fibroid) do exist, but both these methods involve complicated surgical procedures followed by a high rate of complications and a long recovery time.

In order to address these issues, an RF ablation probe that has been used to treat tumors in the human liver by hyperthermia has been demonstrated to substantially shrink or eliminate uterine fibroids.

One such device has been disclosed in U.S. Pat. No. 6,840,935 to Lee. According to the disclosure in that patent, an ablation apparatus with multiple needles or deployable arms is inserted and positioned either proximate to or into a pelvic tumor, the location of which is further confirmed by using a laparoscope and an ultrasound machine. Either electromagnetic energy (and, potentially, other forms of energy) may be delivered through the ablation apparatus to the pelvic tumor to induce hyperthermia and ablate the tumor.

A typical device for ablating pelvic tumors is sold by Rita Medical Systems, Inc. This device consists of a plurality of resilient springy pre-curved RF ablation antennae or stylets housed in a straight lumen. The stylets are ejected in a curved configuration defined by their preformed springy shapes as they exit a sharp-tipped catheter. The deployed antennae with their particular preformed shapes thus can define variously shaped volumes by varying the configuration of the curves which are preformed into the various springy antennae.

SUMMARY OF THE INVENTION

In accordance with the invention, a method and apparatus are provided for the ablation of uterine tissue. According to the present invention, a plurality of conductors are housed within the walls of a cannula, each of which has a proximal end proximate to the proximal end of the cannula and a distal end proximate to the distal end of the cannula.

A plurality of ablation stylets are coupled with each of these conductors such that the distal end of each conductor is connected to the proximal end of a stylet. The conductors and their respective stylets are mounted within the cannula for axial movement and a trocar point defines the distal end of the cannula. A deflection surface can be defined by the metal element defining the trocar point between the trocar point and the proximal end of the cannula. In response to forward axial movement of the stylets, at least some of them are deflected laterally and outwardly, with respect to the cannula axis in different directions along substantially straight paths with the paths defining an ablation volume. The trocar point and the stylets are provided with radio frequency energy, and together form an ablation zone.

In accordance with the invention a uterine fibroid is ablated using a trocar of known dimensional characteristics. The trocar comprises a plurality of ablation stylets mounted for movement from within the trocar to positions extending from the trocar. The trocar is adjustable to assume a plurality of configurations, each of the configurations having the stylets extended to a different extent from the trocar. A region to be ablated is imaged. The region may correspond to all or a portion of a uterine fibroid. The size of the region to be ablated is noted. The size of the region to be ablated is compared to a matrix of known ablation regions, each of the known ablation regions being associated with one of the configurations of the particular trocar of known dimensions, and each of the known ablation regions being associated with a position of the trocar relative to the known ablation region. The region to be ablated is associated with a most nearly matching known ablation region by comparison of the region to be ablated to the known ablation regions. A trocar of the design of the particular trocar is inserted into the uterine fibroid at a position, with respect to the region to be ablated, which more closely matches the position of the particular trocar with respect to the known ablation region. The stylets are deployed from the trocar to an extent corresponding to the configuration associated with the most nearly matching known ablation region.

BRIEF DESCRIPTION THE DRAWINGS

The operation of the invention will become apparent from the following description taken in conjunction with the drawings, in which:

FIG. 2 is a diagram illustrating an embodiment of the method as implemented according to the present invention;

FIG. 3 illustrates another embodiment of the present invention in the context of achieving a larger ablation zone;

FIG. 4 is a diagram illustrating a method to achieve a still larger ablation zone with the deployment of the stylets at a distance of 5 mm into a volume of uterine fibroid tissue;

FIG. 5 illustrates an embodiment of the present invention where the stylets are deployed to 10 mm resulting in a generally egg-shaped volume;

FIG. 6 illustrates the inventive method in the context of achieving an even larger ablation zone;

FIG. 7 illustrates the inventive method in the context of achieving still an even larger ablation zone;

FIG. 8 illustrates the inventive method with the stylets deployed 25 mm into a volume of uterine fibroid tissue;

FIG. 9 illustrates the inventive method with the stylets deployed to 35 mm into the uterine fibroid tissue;

FIG. 10 illustrates the inventive with the stylets at 45 mm; and

FIG. 11 illustrates the inventive method with the stylets deployed to 50 mm, yielding a generally pear-shaped volume.

DETAILED DESCRIPTION OF THE PREFERRED EMBODIMENTS

In accordance with the invention, it has been discovered that trocar point configuration, stylet length and ablation power level may be used to create ablation zones of relatively predictable size and shape.

Figure 1A:
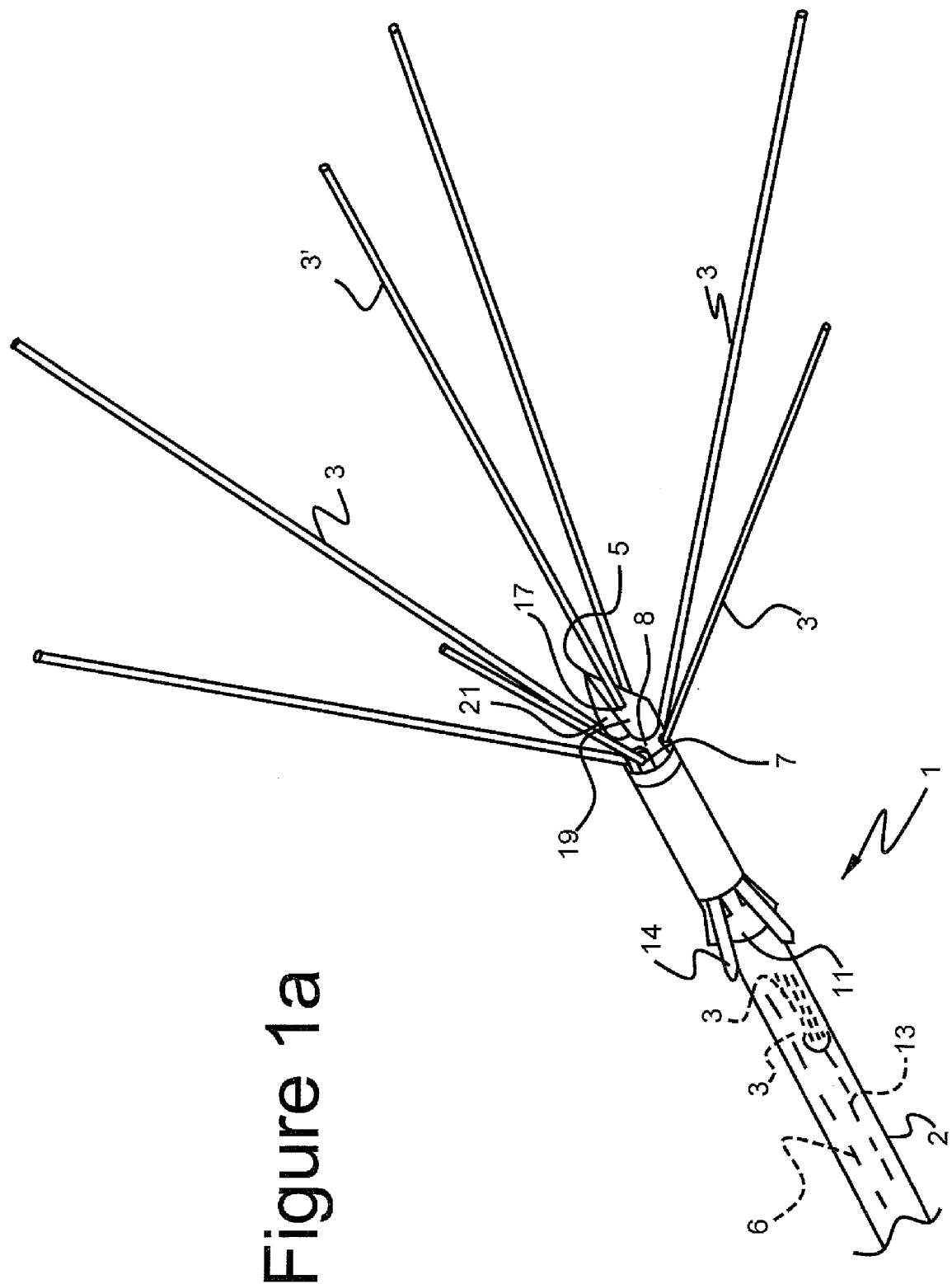
FIG. 1a is a perspective view of a multiple antennae or stylet ablation instrument 1 useful in practicing the inventive method.

FIG. 1a is a perspective view of an ablation instrument 1 with multiple antennae or stylets useful in practicing the inventive method. Ablation instrument 1 with a head end comprising a trocar 1a comprises a cannula 2 which houses a plurality of stylets 3, and, optionally, a plurality of anchors 4. A trocar point 5 is provided at the distal end of cannula 2. At least one conductor 6 is provided within cannula 2. Conductor 6 is electrically coupled to stylets 3 and trocar point 4 and accordingly provides RF energy to stylets 3 and trocar point 5.

In accordance with the invention, stylets 3 and trocar point 5 are electrically coupled to each other and electrically isolated from other exposed portions of ablation instrument 1, such as cannula 2. Each of the stylets are made of thin wire-like tubular members and during the procedure are initially housed entirely within the cannula 2. Stylets 3 are deployed for ablation by being advanced in the forward direction toward the distal end of ablation instrument 1 out from ablation instrument 1 through openings 7. As stylets 3 are advanced through openings 7, they bear against deflection surfaces 8 and move into the positions illustrated in FIG. 1. Deflection surfaces 8 are defined in the metal body which defines trocar point 5 at the distal end of the cannula 2.

During the inventive method, trocar point 5 at the distal end of cannula 2 is used to initially pierce the tissue of the fibroid tumor during use of the inventive ablation device 1. Optionally, a plurality of anchors 9, also housed within ablation instrument 1, may be deployed rearwardly toward the proximal end of ablation instrument 1. During deployment, anchors 4 are deflected by deflection surfaces 11 to move into the positions illustrated in FIG. 1a. After deployment anchors 4 act to prevent rearward movement of trocar point 5 during deployment of stylets 3 out from ablation instrument 1.

Stylets 3 are deployed through the use of a slideably mounted operator member 13 housed within cannula 2 and coupled to an operating handle at its proximal end. Anchors 4 may also be deployed through the use of a slideably mounted operator member (not illustrated) housed within cannula 2 and coupled to an operating handle at its proximal end. The distal end of operator member 13 is coupled to stylets 3 which may thus be advanced an identical distance in unison.

In accordance with the invention, it has been found that by varying the extension of stylets 3 from the trocar point and by varying the power applied to stylets 3 and ablation point 5, the size and shape of the ablation zone may be predictably controlled. For a trocar point of particular dimension, predetermined and relatively uniformly dimensioned and shaped ablation zones may be controllably created.

Figure 1B:
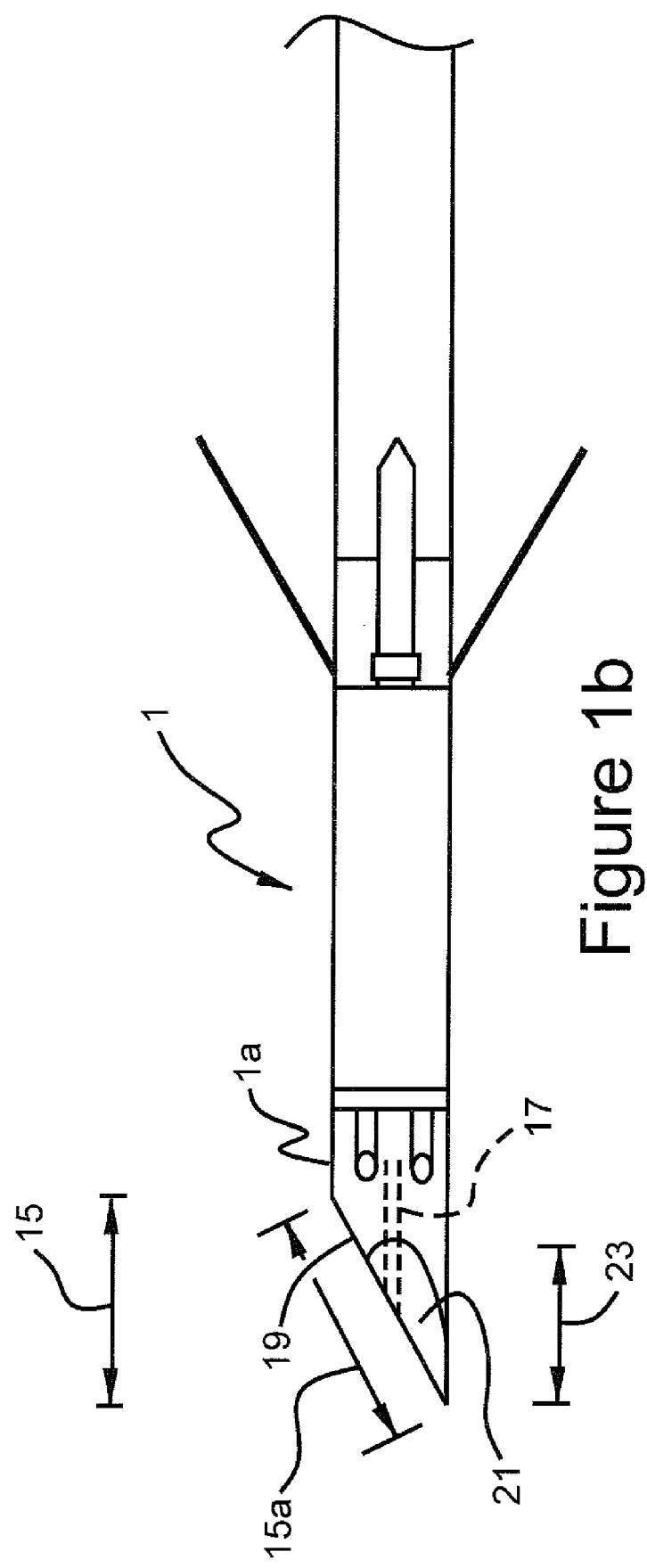
FIG. 1b is a detailed view of a multiple antennae or stylet ablation instrument useful in practicing the inventive method.

In accordance with the invention it is contemplated that three facets cut into a right circular cylindrical metal body with a diameter of 3.5 mm define the shape and size of the trocar point. In accordance with the invention, or a trocar with a diameter of approximately 3.5 mm a height 12 of 8.2 mm has been found to yield excellent results. As shown in FIG. 1b, large facet 19 has a height 15 of approximately 6 mm. Large facet 19 overlies the center of the trocar which defines a cylindrical passage 17 (FIG. 1a-b), through which stylet 3' extends. Large facet 19 has an oblique length 15a of about 7 mm.

Flat facets 21 have a height 23 of approximately 4.5 mm. Facet 19 is accordingly somewhat larger in area as compared to the other two facets 21. In accordance with a preferred embodiment, large flat facet 19 has a length at its widest girth of approximately 3 mm. Facets 21 are approximately 2.6 mm at their widest girth, but are not symmetrical, each having a straight edge which, together with facet 19, forms the point of the trocar. As compared to facets 21, facet 19 extends about 1.5 mm further (along the axis of cannula 2) from point 5 of the trocar toward the proximal end of ablation instrument 1. Facets 21 are symmetrical with respect to each other. The angle between facet 19 and each of the facets 21 is approximately 90°.

While the above-described trocar with the above dimensions as provided excellent results, it is believed that similarly dimensioned pointed trocars, of similar base diameter and length will provide good results.

In accordance with the invention, it is contemplated that the dimensions of the trocar point may vary from the preferred embodiment detailed above. More particularly, it is contemplated that, for the application of the device to fibrous growths (such as uterine fibroids), using materials available today, the diameter of trocar point 5 may vary between 1.5 and 7 mm, although with existing materials, a diameter between 2.75 and 4 mm is preferred and a diameter between 3.2 and 3.7 mm is most preferred. However, to the extent that stronger materials may come to be known, smaller diameter trocars are more desirable, as they cause less trauma to the patient due to the wound created by the introduction of the trocar and cannula into the body of the patient. Conversely, I larger dimensions may be tolerated in some applications than the structure of the present invention can advantageously be used with a larger diameter cannula and trocar.

In accordance with a preferred embodiment, trocar point 5 is made of stainless steel. Stylets 3 are made of tubular nickel titanium alloy having an outer diameter of approximately 0.4 mm. The transducer allows the surgeon to monitor the ablation procedure, and control the extent to which RF energy raises the temperature of the surrounding tissue, and thus control the size of the ablation zone in which substantial or complete cellular necrosis is induced.

EXAMPLE 1

As shown in FIG. 2, when trocar point 5, having the dimensions specified above, is advanced into a volume of uterine fibroid tissue and rf energy applied, an ablation zone 10 having a generally oval-shaped volume may be produced. In accordance with this example of the invention, radio frequency power at a frequency of 460 kilohertz is output into ablation instrument 1, which is deployed without externally extending stylets as illustrated in FIG. 2. The radio frequency power output to trocar point 5 is 15 watts. Radio frequency power output is produced for a period of 15 seconds. The ablation zone 10 which is produced has an axial length 12 of 1 cm and a diameter or width 14 of 0.8 cm. The tip of trocar 1a is located approximately 0.1 cm from the distal edge of ablation volume 10. It is noted that in this configuration, stylets 3 are wholly contained within cannula 2.

As illustrated in FIG. 2, it has accordingly been found that even without extending the stylets, the trocar may be used to create relatively small ablation zones. In accordance with the invention, a trocar having the particular configuration described above yielded excellent results.

EXAMPLE 2

If a larger ablation zone is desired, in accordance with the invention, one may deploy trocar 1a with trocar point 5, and having the dimensions specified above, into a volume of uterine fibroid tissue, to create an ablation zone 20 having a generally global-shaped volume, as illustrated in FIG. 3. In accordance with the invention, radio frequency power at a frequency of 460 kHz is output into ablation instrument 1 and in particular trocar 1a. The radio frequency power output to trocar 1a is 15 watts. Radio frequency power output is produced for a period of 60 seconds. The ablation zone 20 which is produced has a length 22 of 1.5 cm and a width 24 of 1.2 cm. The tip 5 of trocar 1a is located approximately 0.5 cm from the distal edge of ablation volume 10. Ablation zone 20 extends 1.2 centimeters behind trocar point 5. It is noted that in this configuration, stylets 3 are still wholly contained within cannula 2.

EXAMPLE 3

In accordance with the invention, it is also possible to maintain the temperature surrounding ablation stylets 3 for a period of time, as opposed to applying a fixed amount of power to trocar 1a. For example, if a still a larger ablation zone is desired as compared to the ablation zone created in Example 2, in accordance with the invention, one may deploy trocar 1a, having the dimensions specified above, into a volume of uterine fibroid tissue, to create an ablation zone 30, having a generally egg-shaped volume, as illustrated in FIG. 4. In accordance with the invention, radio frequency power at a frequency of 460 kHz is output into ablation instrument 1. Stylets 3 are deployed a distance of 5 mm from the surface of trocar 1a, thus resulting in exposing 5 mm of their length to the uterine fibroid tissue to be ablated.

The radio frequency power output to stylets 3 and trocar 1a may be varied in analog fashion to maintain a temperature of 100° centigrade for a period of 60 seconds. Feedback from the temperature transducers contained within stylets 3 is used to adjust the power output of the RF generator to achieve the desired temperature.

Alternatively, the duty cycle of, for example, a 15 watt radio frequency output coupled to trocar 1a may be varied, for example by turning the output on to begin the heating cycle and reach the desired temperature, shutting it off when a desired temperature of 100° C. is achieved, and turning it on again when the temperature drops below 99.5° C.

The ablation zone 30 which is produced has a length 32 of 2 cm and a width 34 of 1.6 cm. The tip of stylet 3' is located at a distance 36 approximately 0.8 cm from the distal edge of ablation volume 30. Ablation zone 30 extends 1.2 centimeters behind trocar point 5.

It is further noted that in accordance with the present invention, suitable, but smaller ablation zones may be obtained by maintaining temperatures at various points within a range of, for example, 90 to 100° C. In addition, it may be desirable to use higher temperatures or higher powers toward the end of the ablation procedure, depending upon whether there is temperature maintenance as in this example or power maintenance as in Examples 1 and 2.

EXAMPLE 4

If still a larger ablation zone is desired, in accordance with the invention, one may deploy trocar 1a, having the dimensions specified above, into a volume of uterine fibroid tissue, to create an ablation zone 40, having a generally egg-shaped volume, as illustrated in FIG. 5. In accordance with the invention, radio frequency power at a frequency of 460 kHz is output into trocar 1a. Stylets 3 are deployed a distance of 10 mm from the surface of trocar 1a on ablation device 1, thus resulting in exposing 10 mm of their length to the uterine fibroid tissue to be ablated. The temperature of the tissue surrounding stylets 3 and trocar 1a maintained at about 100° using either of the methods detailed above. Temperature is maintained for a period of 30 seconds. The ablation zone 40 which is produced has a length 42 of 25 mm and a width 44 of 23 mm. The tip of stylet 3' is located at a distance 46 approximately 11 mm from the distal edge of ablation volume 40. Similarly, ablation zone 40 extends about 14 mm behind trocar point 5.

EXAMPLE 5

If still a larger ablation zone is desired, in accordance with the invention, one may deploy trocar 1a, having the dimensions specified above, into a volume of uterine fibroid tissue, to create an ablation zone 50, having a generally pear-shaped volume, as illustrated in FIG. 6. In accordance with the invention, radio frequency power at a frequency of 460 kHz is output into ablation instrument 1. Stylets 3 are deployed a distance of 15 mm from the surface of ablation device 1, thus resulting in exposing 15 mm of their length to the uterine fibroid tissue to be ablated. The temperature of the tissue surrounding stylets 3 and trocar 1a is maintained at about 100° using either of the methods detailed above.

Temperature is maintained for a period of 120 seconds. The ablation zone 50 which is produced has a length 52 of 30 mm and a width 54 of 26 mm. The tip of stylet 3' is located at a distance 56 approximately 11 mm from the distal edge of ablation volume 50. Similarly, ablation zone 50 extends about 12 mm behind trocar point 5.

EXAMPLE 6

If an even larger ablation zone is desired, in accordance with the invention, one may deploy trocar 1a into a fibroid to be ablated. Trocar 1a has the dimensions specified above and is positioned in a volume of uterine fibroid tissue to be ablated. Trocar 1a may be driven with RF energy to create an ablation zone 60, having a generally pear-shaped volume, as illustrated in FIG. 7. In accordance with the invention, radio frequency power at a frequency of 460 kHz is output into trocar 1a on ablation instrument 1. Stylets 3 are deployed a distance of 20 mm from the surface of ablation device 1, thus resulting in exposing 20 mm of their length to the uterine fibroid tissue to be ablated. The temperature of the tissue surrounding stylets 3 and trocar 1a is maintained at about 100° using either of the methods detailed above. Temperature is maintained for a period of 180 seconds. The ablation zone 60 which is produced has a length 62 of 36 mm and a width 64 of 31 mm. The tip of stylet 3' is located at a distance 66 approximately 11 mm from the distal edge of ablation volume 60 thus produced. Ablation zone 60 extends about 12 mm behind trocar point 5.

EXAMPLE 7

If still a larger ablation zone is desired, in accordance with the invention, one may deploy trocar 1a, having the dimensions specified above, into a volume of uterine fibroid tissue, to create an ablation zone 70, having a generally pear-shaped volume, as illustrated in FIG. 8. In accordance with the invention, radio frequency power at a frequency of 460 kHz is output into trocar 1a on ablation instrument 1. Stylets 3 are deployed a distance of 25 mm from the surface of trocar 1a, thus resulting in exposing 25 mm of their length to the uterine fibroid tissue to be ablated. The temperature of the tissue surrounding stylets 3 and trocar 1a is maintained at about 100° using either of the methods detailed above. Temperature is maintained for a period of 240 seconds. The ablation zone 70 which is produced has a length 72 of 38 mm and a width 74 of 31 mm. The tip of stylet 3' is located at a distance 76 approximately 10 mm from the distal edge of ablation volume 70. Similarly, ablation zone 70 extends about 12 mm behind trocar point 5.

EXAMPLE 8

If still a larger ablation zone is desired, in accordance with the invention, one may deploy trocar 1a, having the dimensions specified above, into a volume of uterine fibroid tissue, to create an ablation zone 80, having a generally pear-shaped volume, as illustrated in FIG. 9. In accordance with the invention, radio frequency power at a frequency of 460 kHz is output trocar 1a. Stylets 3 are deployed a distance of 35 mm from the surface of trocar 1a, thus resulting in exposing 35 mm of their length to the uterine fibroid tissue to be ablated. The temperature of the tissue surrounding stylets 3 and trocar 1a maintained at about 100° using either of the methods detailed above. Temperature is maintained for a period of 420 seconds. The ablation zone 80 which is produced has a length 82 of 49 mm and a width 84 of 41 mm. The tip of stylet 3' is located at a distance 86 approximately 12 mm from the distal edge of ablation volume 80. Similarly, ablation zone 80 extends about 12 mm. behind trocar point 5.

EXAMPLE 9

If yet a still a larger ablation zone is desired, in accordance with the invention, one may deploy trocar 1a, having the dimensions specified above, into a volume of uterine fibroid tissue, to create an ablation zone 90, having a generally pear-shaped volume, as illustrated in FIG. 10. In accordance with the invention, radio frequency power at a frequency of 460 kHz is output to trocar 1a. Stylets 3 are deployed a distance of 45 mm from the surface of trocar 1a, thus resulting in exposing 45 mm of their length to the uterine fibroid tissue to be ablated. The temperature of the tissue surrounding stylets 3 and trocar 1a maintained at about 100° using either of the methods detailed above. Temperature is maintained for a period of 480 seconds. The ablation zone 90 which is produced has a length 92 of 59 mm and a width 94 of 46 mm. The tip of stylet 3' is located at a distance 96 approximately 11 mm from the distal edge of ablation volume 90. Ablation zone 90 extends 11 mm behind trocar point 5.

EXAMPLE 10

If still a larger ablation zone is desired, in accordance with the invention, one may deploy trocar 1a, having the dimensions specified above, into a volume of uterine fibroid tissue, to create an ablation zone 100, having a generally pear-shaped volume, as illustrated in FIG. 11. In accordance with the invention, radio frequency power at a frequency of 460 kHz is output to trocar 1a. Stylets 3 are deployed a distance of 50 mm from the surface of ablation device 1, thus resulting in exposing 50 mm of their length to the uterine fibroid tissue to be ablated. The temperature of the tissue surrounding stylets 3 and trocar 1a is maintained at about 100° using either of the methods detailed above. Temperature is maintained for a period of 720 seconds. The ablation zone 100 which is produced has a length 102 of 67 mm and a width 104 of 59 mm. The tip of stylet 3' is located at a distance 96 approximately 14 mm from the distal edge of ablation volume 90. Similarly, ablation zone 90 extends about 11 mm behind trocar point 5.

In accordance with the invention, in the power mode typified by the embodiments of FIGS. 2 and 3, the RF generator delivers substantially constant RF power at 460 kHz to all electrodes and the mandrel tip.

In accordance with a preferred embodiment of the invention, a thermocouple is provided at the distal end of each stylet electrode. While all the strategies may be used, in a temperature-controlled ablation, such as Example 3, the system may use the average temperature of the seven thermocouples to control the power output. Alternatively, high and/or low readings may be removed from the calculation.

Optionally, one may employ a power control algorithm which operates differently while it is ramping up to a target temperature, as compared to its operation when it is at or near the target temperature. In accordance with a preferred embodiment of the invention, in ramping mode, a ramping mode power control algorithm applies the full power of the system, reduced by an amount, if any, which causes the system to implement a maximum temperature increase rate of 2° C./second. In accordance with the invention, this ramp rate may be reduced as average temperature measured by the temperature transducers in the probe's ablation stylets approach the target temperature.

When the probe average temperature is below, and within, for example, 0.5° C. of the target temperature, the power control algorithm switches to target power control mode where power is moderated and adjusted to maintain the desired temperature. Target power control delivers power in proportion to the small differences between the thermocouple average and the target temperature.

After the algorithm has switched from ramping to target power control mode, the system may be set to never switch back to ramping mode until the RF power is turned off. That means once target temperature is achieved the amount of RF Power delivered is only to maintain target temperature, in the embodiment of Example 3 and other temperature controlled procedures.

As alluded to above, manual (or power) control mode simply delivers the amount of power to the electrode array and tip that has been set as the target power.

In both temperature and manual modes, the amount of ablation time is controlled by a foot pedal that is used to start and stop the RF delivery.

While illustrative embodiments of the invention have been described, it is noted that various modifications will be apparent to those of ordinary skill in the art in view of the above description and drawings. Such modifications are within the scope of the invention which is limited and defined only by the following claims.

The invention claimed is:

1. A method of ablating a region of a uterine fibroid, comprising:
    (a) employing a trocar comprised of a plurality of ablation stylets, an arrangement of ablation elements, and a trocar point, said trocar being adjustable to assume a plurality of configurations;
    (b) imaging a region to be ablated;
    (c) noting size of the region to be ablated;
    (d) comparing the size of the region to be ablated to a matrix of known ablation regions, each of the known ablation regions being associated with one of the configurations of the trocar, each of the known ablation regions being associated with a position of the trocar relative to the known ablation region;
    (e) associating the region to be ablated with a most nearly matching known ablation region by comparison of the region to be ablated to the known ablation regions;
    (f) inserting the trocar with effectively the same arrangement of ablation elements and trocar point into the uterine fibroid at a location which most closely matches the location of the trocar at the known ablation region; and
    (g) deploying the stylets from the trocar to an extent corresponding to the configuration associated with the most closely matching known ablation region.

2. The method for ablating a uterine fibroid according to claim 1, further comprising:
    (h) insufflating the abdominal cavity of the patient to create an air pocket adjacent to said uterus and within the abdominal cavity; and
    (i) placing a laparoscope in said air pocket in a position to optically image said uterus.

3. The method for ablating a uterine fibroid according to claim 2, wherein the known ablation region is associated with a particular length for each stylet deployment of the trocar and an associated ablation time, and wherein each of the stylets are deployed to the particular length, and further comprising:
    (j) applying RF power to the stylets and the trocar for the associated ablation time; and
    (k) withdrawing said trocar.

4. The method for ablating a uterine fibroid according to claim 3, wherein cautery RF power it is applied to said trocar during withdrawal of said trocar.

5. The method for ablating a uterine fibroid according to claim 3, further comprising:
    (l) noting the orientation of the region to be ablated.

6. The method for ablating a uterine fibroid according to claim 3, wherein a temperature of at least one stylet is measured, and wherein RF power is maintained during the procedure at a level which results in the temperature having an average value in the range between 90° centigrade and 100° centigrade during the ablation procedure.

7. The method for ablating a uterine fibroid according to claim 3, wherein the stylets are deployed between 2.5 and 60.0 mm, wherein RF power is applied for between 15seconds and 900 seconds, wherein a temperature of at least one stylet is measured, and wherein RF power is maintained during the procedure at a level which results in the temperature having an average value in the range between 80° centigrade and 110° centigrade during the ablation procedure.

8. A method of ablating a region of a uterine fibroid, comprising:
    (a) employing a trocar comprised of a plurality of ablation stylets, an arrangement of ablation elements, and a trocar point, said trocar being adjustable to assume a plurality of configurations;
    (b) imaging a region to be ablated;
    (c) noting size of the region to be ablated;
    (d) comparing the size of the region to be ablated to a matrix of known ablation regions, each of the known ablation regions being associated with one of the configurations of the trocar, each of the known ablation regions being associating the region to be ablated with a most nearly matching known ablation region by comparison of the region to be ablated to the known ablation regions;
    (e) associating the region to be ablated with a most nearly matching known ablation region by comparison of the region to be ablated to the known ablation regions;
    (f) inserting the trocar with effectively the same arrangement of ablation elements and trocar point into the uterine fibroid at a location which most closely matches the location of the trocar at the known ablation region; and
    (g) applying a substantially fixed RF power to the trocar for a fixed period of time.

9. A method of ablating an anatomical feature, comprising:
    (a) employing a trocar comprised of a plurality of ablation stylets, an arrangement of ablation elements, and a trocar point, said trocar being adjustable to assume a plurality of configurations;
    (b) imaging a region to be ablated;
    (c) noting size of the region to be ablated;
    (d) comparing the size of the region to be ablated to a matrix of known ablation regions, each of the known ablation regions being associated with one of the configurations of the trocar, each of the known ablation regions being associated with a position of the trocar relative to the known ablation region;
    (e) associating the region to be ablated with a most nearly matching known ablation region by comparison of the region to be ablated to the known ablation regions;
    (f) inserting the trocar with effectively the same arrangement of ablation elements and trocar point into anatomical feature at a location which most closely matches the location of the trocar at the known ablation region; and
    (g) applying a substantially fixed RF power to the trocar for a fixed period of time.

10. The method for ablating an anatomical feature according to claim 9, further comprising noting the orientation of the region to be ablated, wherein each known ablation region is associated with an RF power and application time which is employed during the application of RF power.

11. The method for ablating an anatomical feature according to claim 9, wherein a temperature of at least one stylet is measured, and wherein RF power is maintained during the procedure at a level which results in the temperature having an average value in the range between 90° centigrade and 100° centigrade during the ablation procedure.

12. The method for ablating an anatomical feature according to claim 9, wherein the stylets are deployed between 2.5 and 60.0 mm, wherein RF power is applied for between 15 seconds and 900 seconds, wherein a temperature of at least one stylet is measured, and wherein RF power is maintained during the procedure at a level which results in the temperature having an average value in the range between 80° centigrade and 110° centigrade during the ablation procedure.

* * * * *